(12) United States Patent
Marta et al.

(10) Patent No.: US 11,813,431 B2
(45) Date of Patent: Nov. 14, 2023

(54) FLUID FLOW SENSOR

(71) Applicant: Honeywell International Inc., Morris Plains, NJ (US)

(72) Inventors: Teresa Marta, White Bear Lake, MN (US); Richard Wade, Worthington, OH (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 1085 days.

(21) Appl. No.: 16/370,099

(22) Filed: Mar. 29, 2019

(65) Prior Publication Data

US 2020/0306447 A1 Oct. 1, 2020

(51) Int. Cl.
*A61M 5/168* (2006.01)
*A61M 5/172* (2006.01)

(52) U.S. Cl.
CPC .... *A61M 5/16854* (2013.01); *A61M 5/16877* (2013.01); *A61M 5/16886* (2013.01); *A61M 5/172* (2013.01)

(58) Field of Classification Search
CPC .............. A61M 5/16831; A61M 5/168; A61M 2205/33; A61M 5/16854; A61M 5/16877; A61M 5/16886; A61M 5/172; A61M 2205/3331; A61M 2205/3375; A61M 2205/3561; A61M 5/16859; G01F 23/296; G01F 23/28; G01F 23/22
See application file for complete search history.

(56) References Cited

U.S. PATENT DOCUMENTS

| | | | |
|---|---|---|---|
| 4,722,224 A * | 2/1988 | Scheller | A61M 1/3626 73/599 |
| 5,039,279 A | 8/1991 | Natwick et al. | |
| 5,116,203 A | 5/1992 | Natwick et al. | |
| (Continued) | | | |

FOREIGN PATENT DOCUMENTS

| | | |
|---|---|---|
| CN | 204092729 U | 1/2015 |
| JP | 2002-333434 | 11/2002 |

OTHER PUBLICATIONS

Non-Final Office Action received for U.S. Appl. No. 16/409,496, dated Jan. 27, 2022, 24 pages.
(Continued)

*Primary Examiner* — Jason E Flick
(74) *Attorney, Agent, or Firm* — ALSTON & BIRD LLP (57) ABSTRACT

A fluid flow sensing apparatus and method for detecting pressure and the presence of bubbles within a fluid tube. The flow sensor comprises a housing configured to receive a portion of the tube and to house the pressure sensor and the ultrasonic transmitter. The pressure sensor is positioned adjacent the tube and is configured to receive a pressure sensor signal, which correlates to a detected pressure differential within the tube. An internal controller transmits a drive signal to the ultrasonic transmitter, which emits ultrasonic waves through a portion of the tube and to the pressure sensor. The pressure sensor receives both the ultrasonic waves and a pressure sensor signal, and subsequently transmits an output signal to the internal controller. In the presence of a pressure differential or a bubble within the tube, the output signal will exhibit a DC shift or a distortion of its signal characteristics, respectively.

17 Claims, 8 Drawing Sheets

(56) References Cited

U.S. PATENT DOCUMENTS

| | | | |
|---|---|---|---|
| 5,661,245 A * | 8/1997 | Svoboda | A61M 5/16854 73/726 |
| 7,661,294 B2 * | 2/2010 | Dam | G01N 29/02 73/598 |
| 8,286,505 B2 | 10/2012 | Wade | |
| 8,770,010 B1 | 7/2014 | Shapiro | |
| 10,046,112 B2 | 8/2018 | Druklu et al. | |
| 11,517,670 B2 | 12/2022 | Brown et al. | |
| 2002/0104370 A1 | 8/2002 | Steger et al. | |
| 2005/0145009 A1 * | 7/2005 | Vanderveen | A61M 5/16854 73/1.57 |
| 2005/0212869 A1 | 9/2005 | Ellson et al. | |
| 2008/0066557 A1 | 3/2008 | Yoshida | |
| 2011/0130741 A1 | 6/2011 | Miles et al. | |
| 2011/0152642 A1 | 6/2011 | Robinson | |
| 2013/0296823 A1 | 11/2013 | Melker et al. | |
| 2015/0153262 A1 | 6/2015 | Hies et al. | |
| 2015/0224254 A1 | 8/2015 | Sullivan et al. | |
| 2016/0045400 A1 | 2/2016 | Hudson | |
| 2018/0306559 A1 | 10/2018 | Eberhart | |
| 2018/0306659 A1 | 10/2018 | Wade et al. | |
| 2018/0306660 A1 | 10/2018 | Wade et al. | |

OTHER PUBLICATIONS

Extended European Search Report for Patent Application No. 20165405.0 dated Jul. 2, 2020, 8 pages.
Communication Pursuant to Article 94(3) issued in European Application No. 20165405.0 dated Nov. 19, 2021, 3 pages.
Non-Final Office Action received for U.S. Appl. No. 16/409,496, dated Jul. 15, 2021, 21 pages.
Non-Final Rejection dated Mar. 31, 2023 for U.S. Appl. No. 18/052,166, 13 page(s).
Andy Walker Brown et al., U.S. Appl. No. 18/052,166 for "Fluid Sensor", filed Nov. 2, 2022.
Examiner Interview Summary Record (PTOL - 413) dated Oct. 21, 2021 for U.S. Appl. No. 16/409,496.
Final Rejection dated Apr. 27, 2021 for U.S. Appl. No. 16/409,496.
Non-Final Rejection dated Jan. 27, 2022 for U.S. Appl. No. 16/409,496.
Non-Final Rejection dated Jul. 15, 2021 for U.S. Appl. No. 16/409,496.
Non-Final Rejection dated Nov. 23, 2020 for U.S. Appl. No. 16/409,496.
Notice of Allowance and Fees Due (PTOL-85) dated Aug. 3, 2022 for U.S. Appl. No. 16/409,496.
Office Action Appendix dated Oct. 21, 2021 for U.S. Appl. No. 16/409,496.
Notice of Allowance and Fees Due (PTOL-85) dated Jul 31, 2023 for U.S. Appl. No. 18/052,166, 2 page(s).
Notice of Allowance and Fees Due (PTOL-85) dated Jun 2, 2023 for U.S. Appl. No. 18/052,166, 10 page(s).
Notice of Allowance and Fees Due (PTOL-85) dated Sep 5, 2023 for U.S. Appl. No. 18/052,166, 2 page(s).

* cited by examiner

FLUID FLOW SENSOR

BACKGROUND

Fluid flow sensors are used today to characterize flow in a wide variety of applications including, for example, medical applications. In particular, fluid flow sensors may be incorporated as components of safety measures associated with intravenous infusions, a treatment measure in the daily routine of modern hospitals. Intravenous infusions utilize infusion pumps to administer fluids such as nutrients, blood, and medication intravenously to patients in controlled amounts.

Accordingly, a need exists for improved sensors characterized by a low error rate and minimized footprint.

BRIEF SUMMARY

Various embodiments relate to a fluid flow sensor contained within a singular housing that is configured to detect pressure changes and to detect the presence of air bubbles in-line while minimizing both the error rate and the footprint of the sensor.

Various embodiments are directed to a fluid flow sensor comprising an ultrasonic transmitter configured to emit ultrasonic signals through an emitting face and a pressure sensor configured to detect pressure changes through a receiving face, wherein the pressure sensor may be spaced apart from the ultrasonic transmitter to define a gap. The emitting face of the ultrasonic transmitter and the receiving face of the pressure sensor may collectively define a gap. The gap may be adjustable to compress a fluid delivery conduit within the gap and between the emitting face of the ultrasonic transmitter and the receiving face of the pressure sensor. The pressure sensor may be configured to detect a change in pressure within a fluid delivery conduit compressed within the gap and monitor ultrasonic signals received from the ultrasonic transmitter to detect bubbles flowing through the fluid delivery conduit compressed within the gap.

In various embodiments, the fluid flow sensor may comprise an ultrasonic transmitter configured to emit ultrasonic signals through an emitting face and a pressure sensor configured to detect pressure changes through a receiving face, wherein the emitting face of the ultrasonic transmitter is spaced apart from the receiving face of the pressure sensor to collectively define a gap configured to receive a fluid delivery conduit therein; and wherein the pressure sensor is configured to detect a change in pressure within a fluid delivery conduit positioned within the gap; and receive ultrasonic signals from the ultrasonic transmitter to detect bubbles flowing through the fluid delivery conduit positioned within the gap. In various embodiments, the fluid flow sensor may further comprise a housing, wherein the housing comprises an exterior housing portion and an interior housing portion, and wherein the ultrasonic transmitter and the pressure sensor are enclosed within the interior housing portion. In various embodiments, the housing may be blow-molded, injection molded, or manufactured by any other suitable means. In various embodiments, the interior housing portion further defines a channel configured to secure at least a portion of the fluid delivery conduit within the interior portion of the housing and wherein at least a portion of the channel defines the gap. Further, in various embodiments, a portion of the fluid delivery conduit positioned within the gap is compressed such that the at least substantially all of the receiving face of the pressure sensor is engaged by a portion of the fluid delivery conduit.

In various embodiments, the pressure sensor may comprise a pressure sensing element mounted to a substrate and a force transmitting member positioned adjacent to the pressure sensing element, wherein the force transmitting member transmits a force applied to the front side of the force transmitting member to the front side of the pressure sensing element. In various embodiments, the force transmitting member may be a gel.

In various embodiments, an internal controller may be configured for wireless communication of an output signal. Further, in various embodiments, the ultrasonic transmitter is configured to receive a drive signal from an internal controller, wherein the drive signal comprises at least one of an AC component or a DC component. In various embodiments the ultrasonic transmitter may comprise a piezoelectric ultrasonic transducer, and may further comprise an ultrasonic generator. In various embodiments, the fluid flow sensor may be configured to detect a change in pressure within a fluid delivery conduit based at least in part on a detected shift in a received signal. Further, in various embodiments, the fluid flow sensor may be configured to detect the presence of an air bubble within the fluid delivery conduit based at least in part on a detected change in ultrasonic signal amplitude received from the ultrasonic transmitter.

Various embodiments may be directed to a method of detecting occlusion and the presence of bubbles within a fluid delivery conduit, the method comprising: detecting a change in pressure within a fluid delivery conduit based at least in part on a detected shift in a received signal and detecting the presence of an air bubble within the fluid delivery conduit based at least in part on a detected change in ultrasonic signal amplitude received from the ultrasonic transmitter, wherein a signal output by the pressure sensor comprises both an AC and a DC component. In various embodiments, the method may further comprise emitting ultrasonic signals from an ultrasonic transmitter, through the fluid delivery conduit, and to a pressure sensor aligned with the ultrasonic transmitter on an opposite side of the fluid delivery conduit and configured to receive the ultrasonic signals emitted from the ultrasonic transducer. In various embodiments, the signal emitted from the ultrasonic transmitter comprises an AC signal. In various embodiments, a DC shift in the pressure sensor's output signal corresponds to a change in pressure within the fluid delivery conduit. In various embodiments, the method may further comprise communicating the pressure sensor's output signal to one or more external devices. In various embodiments, an internal controller is configured for wireless communication of an output signal.

BRIEF DESCRIPTION OF THE DRAWINGS

Reference will now be made to the accompanying drawings, which are not necessarily drawn to scale, and wherein.

DETAILED DESCRIPTION

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Overview

Described herein is a fluid flow sensor configured to characterize and monitor the flow of fluid through a fluid delivery conduit. In an example implementation, a fluid flow sensor as discussed herein may be utilized to monitor fluid flow in tubes utilized in a medical environment (e.g., blood flow tubes, fluid delivery tubes, and/or the like). The fluid flow sensor discussed herein may be configured to utilize non-invasive ultrasonic technology to detect the presence of air bubbles within a tube. Such configurations are capable of point and continuous sensing, able to detect small bubbles, efficient with respect to power consumption, durable, compatible with a variety of tubing materials, and less sensitive to particle accumulation. The fluid flow sensor of certain embodiments described herein exhibits the aforementioned advantages, while further comprising components that enable both low-cost production and a decreased sensor footprint. Critically, a minimized sensor footprint may, in certain applications (e.g., medical infusion), enable monitoring at a point of entry into a patient's body, which may result in a more accurate dosage delivery.

As described herein, the fluid flow sensor may detect pressure changes within the tube, which may be caused by, for example, an occlusion causing a decrease in liquid fluid flow due to a blockage within the tube (which may be detected in light of a decrease in pressure within the tube). The sensor may also detect bubbles, which as described herein encompass a volume of gas having a surface defined as an interface between the gaseous fluid (within the interior of the bubble) and a liquid fluid (at least partially surrounding the exterior of the bubble).

Fluid flow sensors as discussed herein comprise both a pressure sensor and an ultrasonic transmitter, and characterize the flow in a tube positioned between the pressure sensor and the ultrasonic transmitter by measuring the in-line fluid pressure and detecting in-line air bubbles. The fluid flow sensor further comprises a housing configured receive at least a portion of a fluid delivery conduit, and to house the pressure sensor and the ultrasonic transmitter. Within the housing, the pressure sensor is positioned on one side of the fluid delivery conduit and the ultrasonic transmitter is positioned across from the pressure sensor on an opposite of the tubing; the two elements are aligned so as to face one another such that the ultrasonic transmitter emits ultrasonic signals through the fluid delivery conduit and into the face of the pressure sensor. To ensure the accuracy of the pressure sensor output, the portion of the fluid delivery conduit enclosed within the housing may be compressed such that substantially all of the face of the pressure sensor is in contact with the wall of the fluid delivery conduit. Alternatively, the pressure sensor and the ultrasonic transmitter may be positioned adjacent to one another on the same side of the fluid delivery conduit. The two elements may be aligned so as to face into the fluid delivery conduit in substantially the same direction such that the ultrasonic transmitter may emit ultrasonic signals through the fluid delivery conduit and into a reflector element positioned to reflect the emitted signals back through the fluid delivery conduit and into the face of the pressure sensor.

The pressure sensor may comprise a pressure sensing element, which may, for example, be embedded in a coupling gel or some other force transmitting member such that low frequency, pressure-related signals detected as occurring within the tube (e.g., caused by occlusion) are sensed by the pressure sensing element as the gel transmits the signal from the tube (e.g., from the surface of the tube in contact with a surface of the force transmitting member). The gel also acts as a high pass filter allowing high frequency signals to pass through without causing any substantial deflection within the gel. Such a configuration allows for the ultrasonic transmitter to emit high frequency signals through the tube and through the gel before reaching the pressure sensing element, thereby enabling the sensor's bubble detection functionality. When a bubble is present within the fluid flow, at least a portion of the high frequency signal that is emitted from the ultrasonic transmitter is reflected off the surface of the bubble (and generally away from the pressure sensor), thus creating a change in the signal received by the pressure sensor—which may be correlated to the detection of the presence of a bubble in the tube. The fluid flow sensor of certain embodiments detects AC and DC signal components of a signal transmitted from the ultrasonic transmitting member to characterize the in-line flow: the DC component is utilized to detect changes in pressure within the tube (e.g., which may be caused by occlusion), while the AC component is utilized for the bubble detection. As designed, the fluid flow sensor effectively reduces error rate by utilizing a dual sensor configuration (i.e. the simultaneous AC and DC signal components) to be used to compensate for inaccurate variations in the sensor's reading resulting from drifts in the acoustic baseline due to unwarranted changes in contact force (e.g., tubing deformation, temperature change, fluid pressure, etc.).

Housing/Sensor Construction

Figure 1:
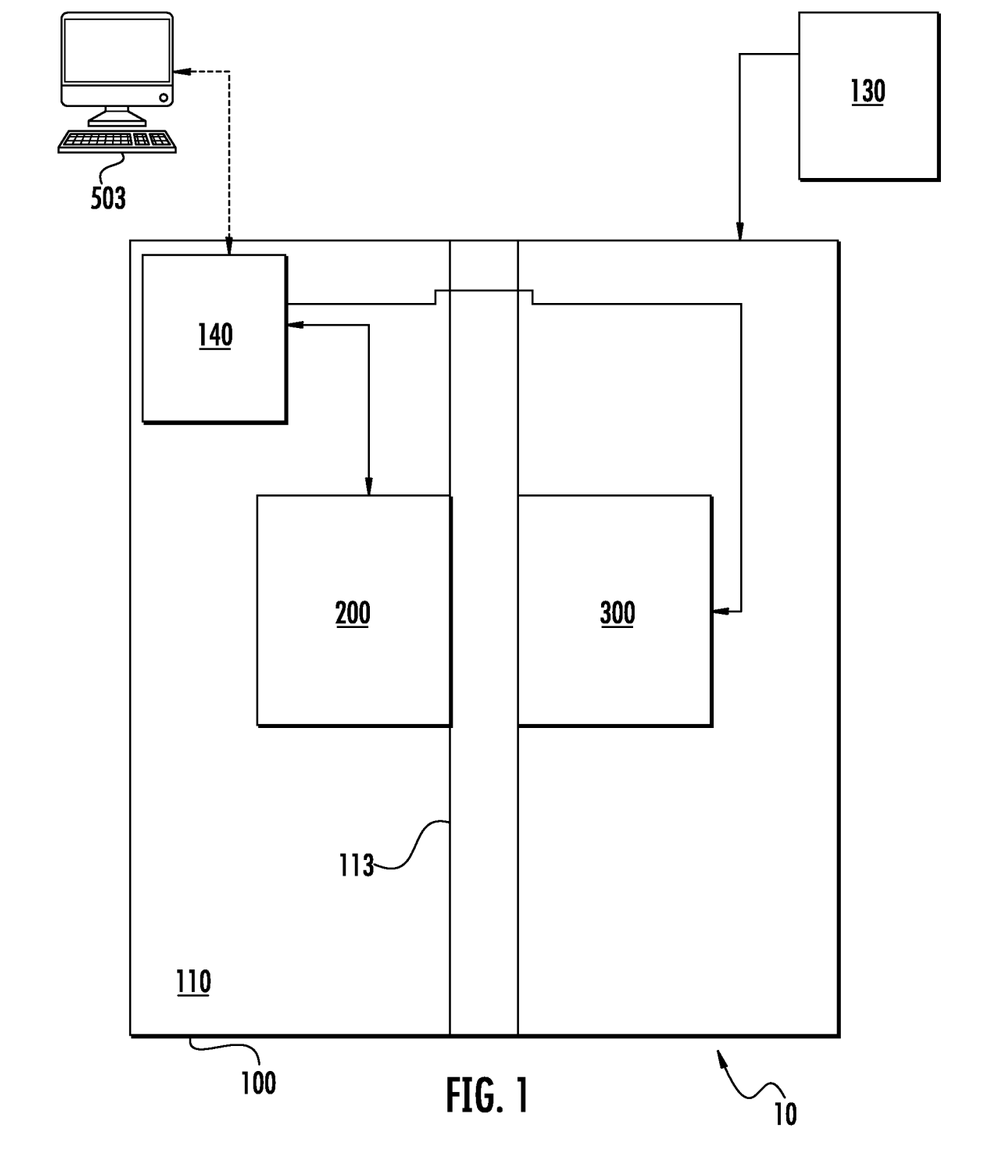
FIG. 1 schematically illustrates communication among various components in accordance with some embodiments discussed herein.
Figure 2:
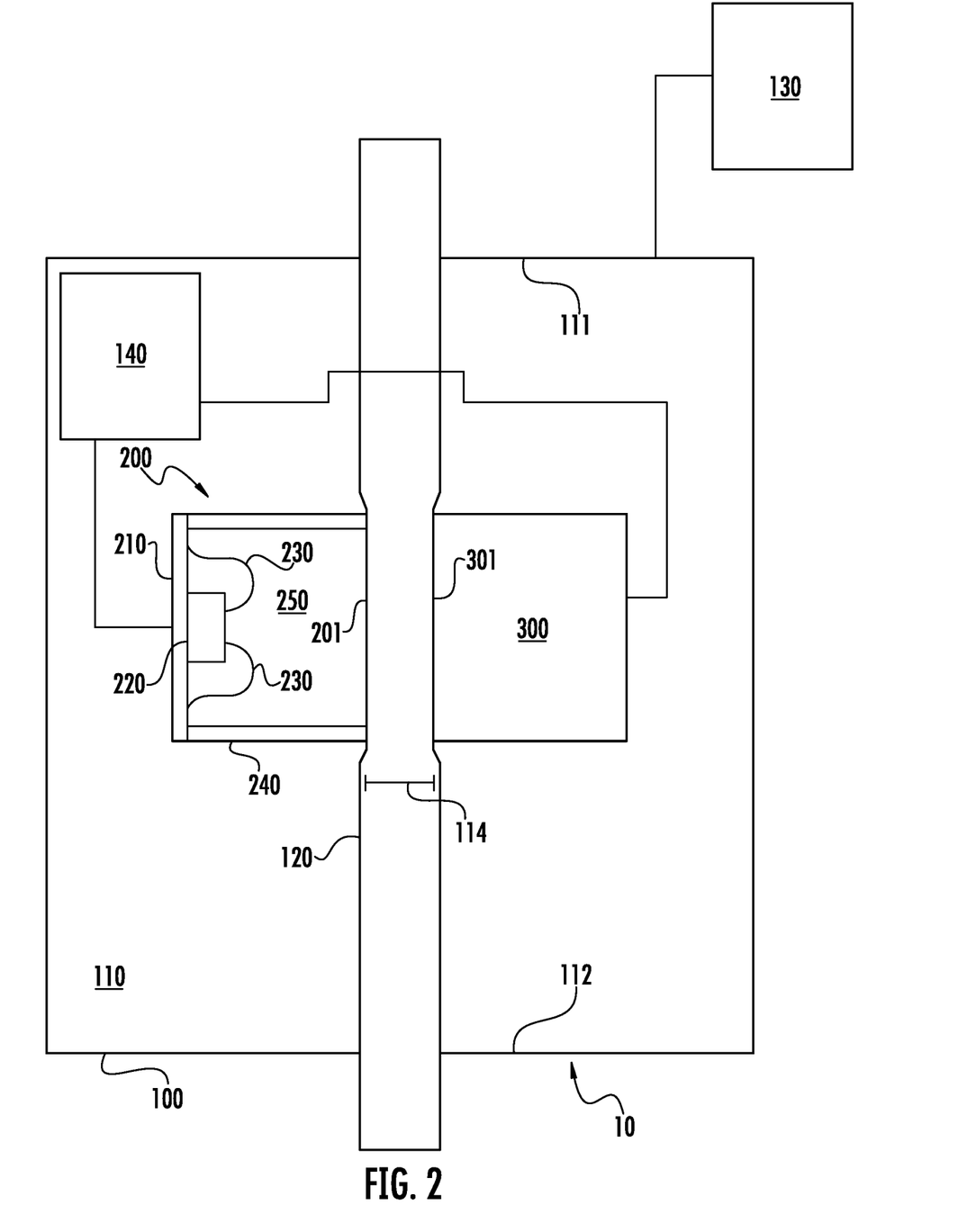
FIG. 2 schematically illustrates an exemplary sensor in accordance with various embodiments.
Figure 3:
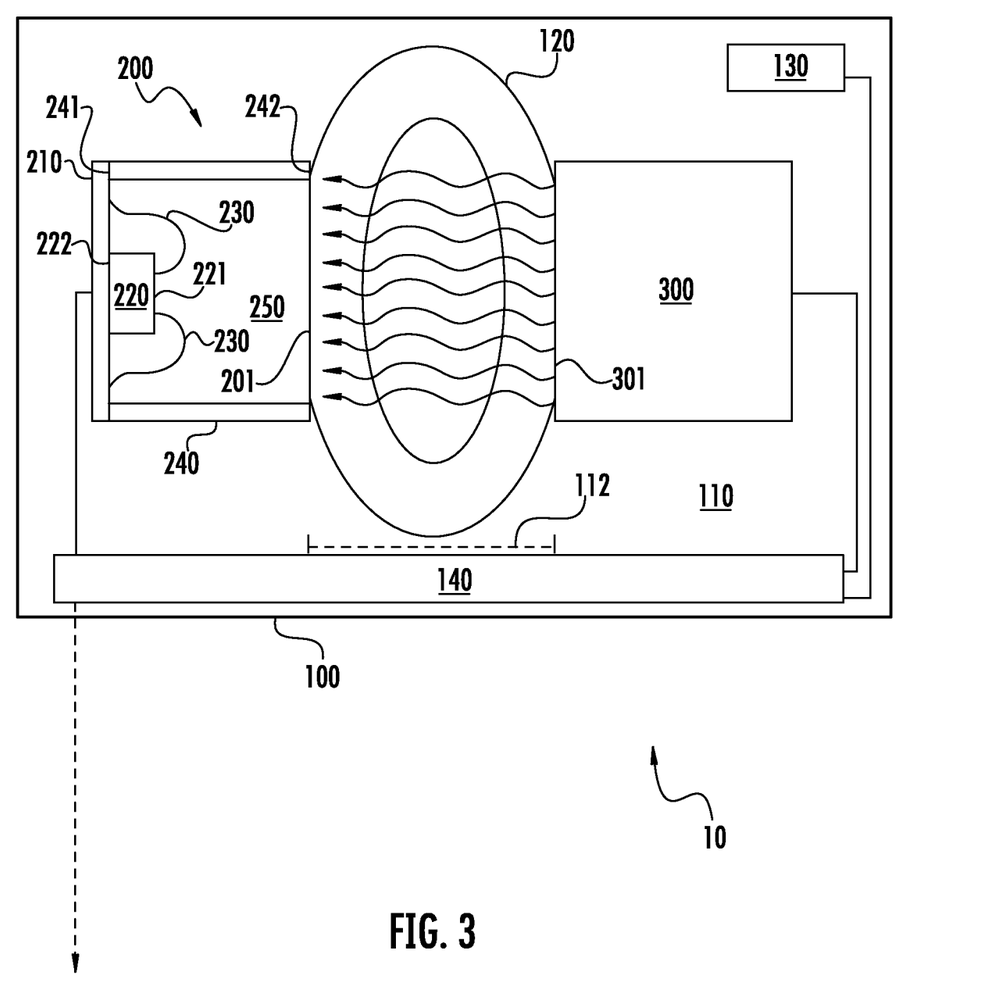
FIG. 3 illustrates a cross-sectional view of an exemplary apparatus as described herein without a bubble in the fluid delivery conduit.

As shown in FIGS. 1-3, the fluid flow sensor 10 comprises a housing 100. The housing 100 defines the exterior of the fluid flow sensor 10 and may have a height, length, and a width, wherein the length of the housing 100 is defined by the distance between a first end and a second end. As illustrated in FIG. 1, the housing may further comprise a channel 113 extending from the first end of the housing 100 to the second end and configured to receive and secure at least a portion of a fluid delivery conduit. Housing 100 may be configured to enclose both the pressure sensor 200 and the ultrasonic transmitter 300 within the interior portion of the housing. The pressure sensor 200 and the ultrasonic transmitter 300 are each coupled to an interior portion of the housing 110 and are spaced apart within the interior portion of the housing 110 to define a gap 114 between the two elements. In various embodiments, the width of the gap 114 may be substantially equal to the width of the channel 113 and may run parallel to (and/or coextensive with) at least a portion of the channel 113. The pressure sensor 200 and the ultrasonic transmitter 300 of the illustrated embodiment are aligned within the housing 100 so as to face one another; that is, the emitting face of the ultrasonic transmitter 301 should be facing toward the receiving face of the pressure sensor 201 such that high frequency waves generated by the ultrasonic transmitter 300 and emitted from the emitting face of the ultrasonic transmitter 301 travel towards the receiving face of the pressure sensor 201. In such an exemplary configuration, the pressure sensor 200 and the ultrasonic transmitter 300 may be arranged to face a direction perpendicular to the length of the channel 113, and may define at least a portion of the channel 113.

In various embodiments, the fluid delivery conduit may have a length, and a diameter, and may comprise an outer circumferential wall, an inner circumferential wall, and a wall thickness extending between the outer circumferential wall and the inner circumferential wall; and an interior channel within the inner wall configured to direct the flow of fluid from one location to a second location. The fluid delivery conduit may comprise a resilient material (e.g., a silicone material, a polyvinyl chloride material, and/or the like).

The housing 100 may be configured to receive at least a portion of a fluid delivery conduit 120 through the channel. A portion of fluid delivery conduit 120 may extend from a first end of the housing 111 to a second end of the housing 112. The fluid delivery conduit 120 may be positioned within the channel 113 such that it runs parallel to and intersects the gap 114. In such a configuration, at least a portion of the fluid delivery conduit 120 is between the pressure sensor 200 and the ultrasonic transmitter 300. In such an exemplary configuration, the pressure sensor 200 and the ultrasonic transmitter 300 may be arranged to face a direction perpendicular to the length of the fluid delivery conduit 120. Further, the pressure sensor 200 and the ultrasonic transmitter 300 may be centered at the same position along the length of the fluid delivery conduit such that the gap 114 between the two elements is substantially perpendicular to the length of the fluid delivery conduit.

As described above and as illustrated in FIGS. 2-4, at least a portion of the fluid delivery conduit 120 may be positioned between and adjacent to the pressure sensor 200 and the ultrasonic transmitter 300 such that when the ultrasonic transmitter 300 emits signals (e.g., high frequency ultrasonic signals) in the direction of the pressure sensor 200, the signals pass through a cross-section of the fluid delivery conduit 120. The housing 100 may be adjustably configured such that the width of the gap 114 between the pressure sensor 200 and the ultrasonic transmitter 300 may be smaller than the diameter of fluid delivery conduit 120, thereby causing a compression force to be applied to a portion of the outer wall of the fluid delivery conduit 120 secured within the gap 114. The compression force may be applied in a direction perpendicular to the length of the fluid delivery conduit 120 such that the outer wall of the fluid delivery conduit 120 is pressed against the receiving face of the pressure sensor 201. In such an exemplary configuration, the applied compression force may be sufficient to cause substantially all of the receiving face of the pressure sensor 201 to be engaged by the compressed outer wall of the fluid delivery conduit 120. In various embodiments, the fluid flow sensor 10 may be further configured to monitor a compressive force applied to a portion of the fluid delivery conduit 120 positioned between the receiving face of the pressure sensor 201 and the ultrasonic transmitter 300 (e.g., using an ancillary pressure sensor). The measured compressive force applied to the portion of the fluid delivery conduit 120 may be utilized in certain embodiments to calibrate pressure sensor 200 readings of pressure within the fluid delivery conduit 120. In other embodiments, the fluid flow sensor 10 may be separately calibrated for pressure sensor 200 readings of pressure within the fluid delivery conduit 120.

In some embodiments, the fluid flow sensor 10 may be connected to a power supply 130 configured to receive power and power the fluid flow sensor. As non-limiting examples, the power supply 130 may comprise one or more batteries, one or more capacitors, one or more constant power supplies (e.g., a wall-outlet), and/or the like. In some embodiments, as shown in FIG. 2, the power supply 130 may comprise an external power supply positioned outside of the housing 100 and configured to deliver alternating or direct current power to the fluid flow sensor 10. Further, in some embodiments, as illustrated in FIG. 3, the power supply 130 may comprise an internal power supply, for example, one or more batteries, positioned within the housing 100.

Figure 4:
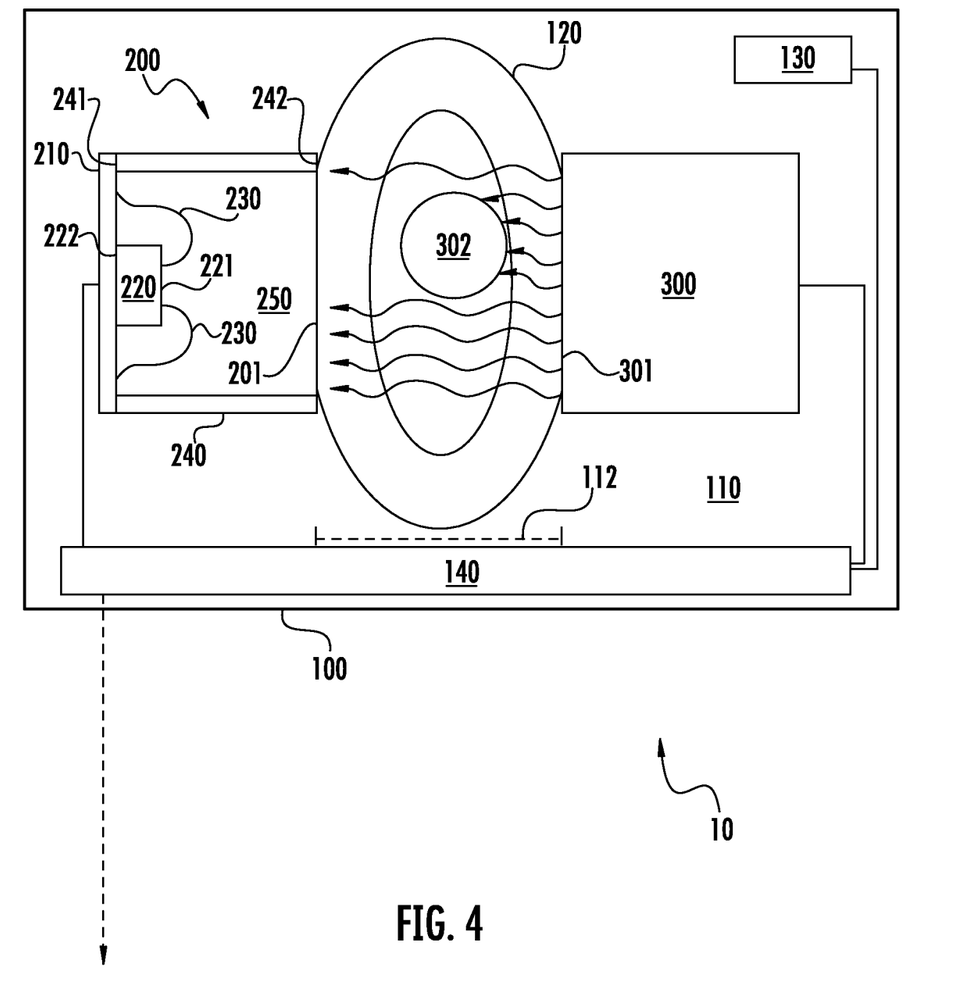
FIG. 4 illustrates a cross-sectional view of an exemplary apparatus as described herein with a bubble in the fluid delivery conduit.

In various embodiments, power may be supplied to internal controller 140 to enable distribution of power to the various components described herein. In some embodiments, each of the components of the fluid flow sensor 10 may be connected to internal controller 140 (e.g., for electronic communication), which may be configured to facilitate communication and functional control therebetween. In various embodiments, the internal controller 140 may comprise one or more of a processor, memory, a communication module, and an on-board display 150. For example, the internal controller 140 may comprise a driving circuit and a signal processing circuit. In various embodiments, the internal controller 140 may be configured to power the pressure sensor 200 and/or receive an output signal from the pressure sensor 200. In various embodiments, the internal controller 140 may be configured to power the ultrasonic transmitter 300 and/or transmit a drive signal to the ultrasonic transmitter 300. In various embodiments, as shown in FIGS. 3 and 4, the internal controller may be configured to transmit output signals out to external components via universal serial bus (USB) or any other wired connection. In various embodiments, an on-board display may be configured to display a variety of signals transmitted from or received by the internal controller 140, and/or the like. In various embodiments, the internal controller may be embodied as a single chip (e.g., a single integrated-circuit chip) configured to provide power signals to both the pressure sensor 200 and the ultrasonic transmitter 300, to receive and process the output signal from the pressure sensor 200, and/or to compensate for any detected changes in environmental factors such as, for example, temperature, flow, or pressure within the fluid delivery conduit 120. Such a configuration may be desirable to minimize production costs and reduce the physical footprint of the fluid flow sensor 10.

Figure 5:
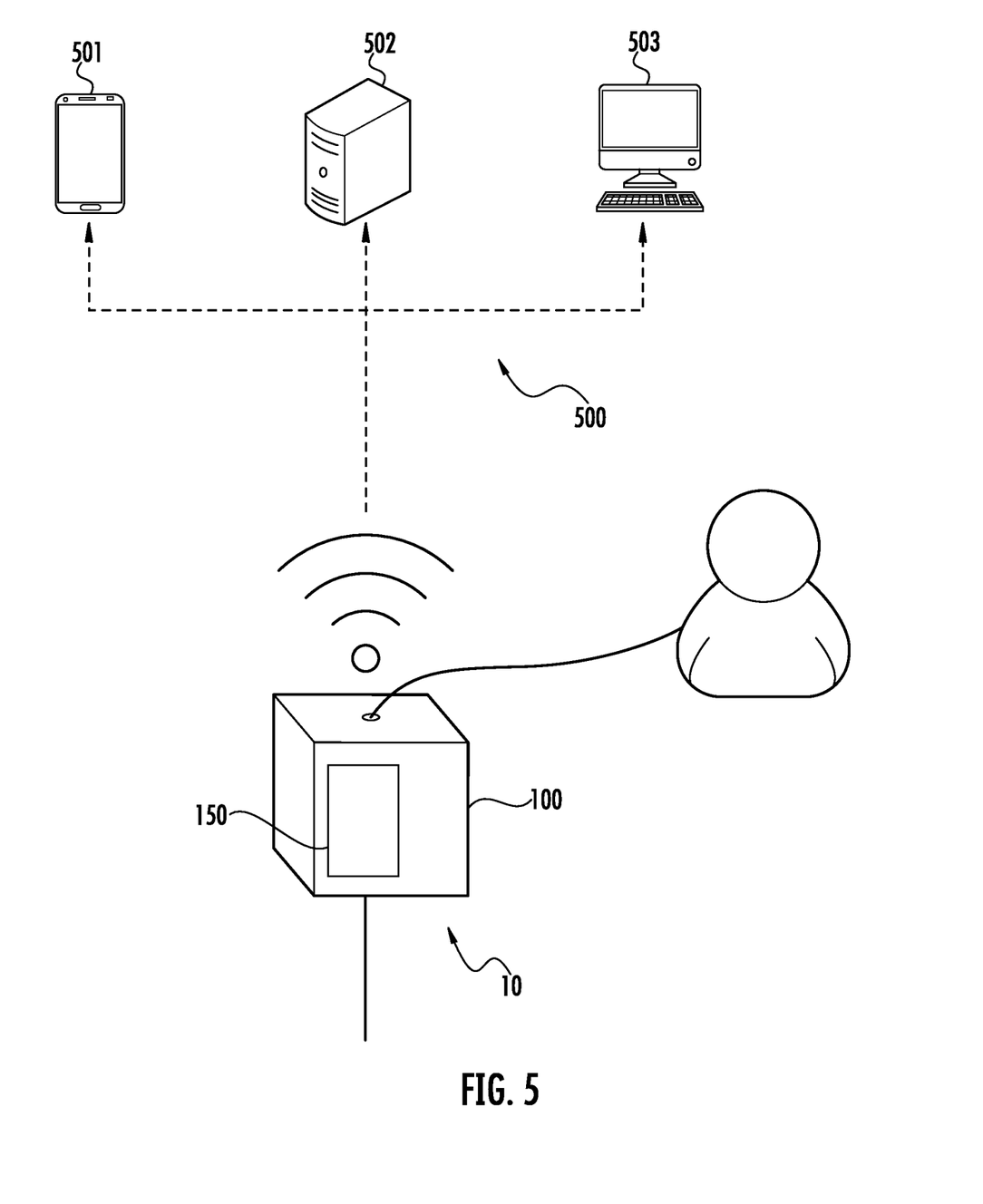
FIG. 5 illustrates data flows among components in accordance with some embodiments discussed herein.

As described above and as will be appreciated based on this disclosure, various embodiments may be configured in various forms including with portions of the fluid flow sensor 10 shown in FIG. 5 being remote from the apparatus. In various embodiments, all of the components necessary to characterize the flow through a fluid delivery conduit 120 may be integrated into a single housing 100. In various embodiments, the internal controller 140 may be configured to communicate with a variety of external devices via Bluetooth™ Bluetooth Low Energy (BTLE), Wi-Fi™, or any other wireless connection. As shown in FIG. 5, the internal controller may be configured so as to enable wireless communication within an Internet-of-Things (IoT) network 500 to a variety of wirelessly enabled devices (e.g., a user mobile device 501, a server 502, a computer 503, and/or the like).

Pressure Sensor

As shown in FIGS. 1-4, the fluid flow sensor 10 may comprise a pressure sensor 200. The pressure sensor may be embodied as a pressure sensor such as that described in U.S. Patent Publ. No. 2018/0306659, which is incorporated herein by reference in its entirety. In various embodiments, the pressure sensor 200 may comprise a printed circuit board 210, a pressure sensing element 220, a sidewall 240, and a force transmitting member 250. As described above, the pressure sensor may be positioned within the housing 100 and coupled to an interior portion of the housing 100. The pressure sensor 200 may further comprise a receiving face 201, which may be, for example, either a flat, convex, or concave surface. The pressure sensor may be arranged such that the receiving face 201 is aligned with and facing the emitting face of the ultrasonic transmitter 301. The receiving face of the pressure sensor 201 may be spaced apart from the emitting face of the ultrasonic transmitter 301 at a distance defining the gap 114.

The substrate 210 of the pressure sensor 200 may be any type of printed control board (PCB), a ceramic substrate, or other suitable substrate configuration. In some embodiments, the substrate 210 may be a thick film printed ceramic board, however other circuit board configurations may be utilized in other embodiments. In one example, the substrate 210 may be made, at least in part, of FR 4 laminate and/or other material. In various embodiments, the substrate 210 may have one or more electronic components thereon and/or pads for connecting to electronic components of a device in which the pressure sensor 200 may be inserted or with which the pressure sensor 200 may be used. In one example, the substrate 210 may include an application specific integrated circuit (ASIC) that may be attached to the substrate 210. Such an ASIC may be electrically connected to the substrate 210 via wire bonds, bump bonds, electrical terminals, and/or any other suitable electrical connections. Additionally or alternatively, the substrate 210 may include one or more conductive pads for engaging circuitry and/or electronic components in communication with a remote processor or the like.

Further, the substrate 210 may include one or more processing electronics and/or compensation circuitry (e.g., which may or may not include an ASIC). Such processing electronics may be electrically connected to terminals of the pressure sensing element 220, an ASIC (if present), and/or electrical terminals to process electrical signals from the pressure sensing element 220 and/or to transfer outputs from the pressure sensing element 220 to electronic components of one or more devices used in conjunction with the pressure sensor 200. In some instances, the substrate 210 may include circuitry that may be configured to format one or more output signals provided by the pressure sensing element 220 into a particular output format. For example, circuitry of the substrate 210 (e.g., circuitry on one or more of sides of the substrate 210) may be configured to format the output signal provided by pressure sensing element 220 into a ratio-metric output format, a current format, a digital output format and/or any other suitable format. In some cases, the circuitry of the substrate 210 may be configured to regulate an output voltage. Circuitry on the substrate 210 for providing a ratio-metric (or other) output may include traces and/or other circuitry that may serve as a conduit to test pads, and/or for providing the ratio-metric (or other) output to one or more electrical terminals facilitating electrical connections with electronic components of one or more devices used with the pressure sensor 200.

The pressure sensing element 220 of the pressure sensor 200 may be configured in any manner and may have a first side 221 (e.g., a front side) and a second side 222 (e.g., a back side). In some cases, the pressure sensing element 220 may include a micro-machined pressure sense die that includes a sense diaphragm. In various embodiments, the pressure sensing element 220 may be back-side mounted on the substrate 210 with the second side of the pressure sensing element 222 facing the substrate 210 and may be configured to perform top-side sensing (e.g. sensing with the first side of the pressure sensing element 221). In a pressure sensing element 220 configuration, the top-side sensing may be when a sensed media either directly or indirectly (e.g., through the force transmitting member 250 or other intermediary) interacts with a top side of the pressure sensing element 221. Back-side mounting the pressure sensing element 220 to the substrate 210 may facilitate creating a robust pressure sensor 200 because any sensed media acting on the pressure sensing element 220 may act to push the pressure sensing element 220 against the substrate 210. Although the pressure sensing element 220 may be described herein as being back-side mounted to the substrate 210, it is contemplated that the pressure sensing element 220 may be mounted relative to the substrate 210 in one or more other configurations. For example, the pressure sensing element 220 may be front side mounted or mounted in any other suitable manner. Further, the pressure sensing element 220 may be electrically connected to the substrate 210 in one or more manners. In various embodiments, wire bonds 230 may be utilized to electrically connect the pressure sensing element 220 to the substrate 210. The wire bonds 230 may have a first end connected to a bond pad of the pressure sensing element 220 and another end connected to a bond pad of the substrate 210. Additionally or alternatively, the pressure sensing element 220 may be electrically connected to the substrate 210 via bump bonds and/or in any other suitable manner.

The sidewall 240 of the pressure sensor 200 may extend from a first end 241 to a second end 242. In various embodiments, the sidewall 240 may entirely or at least partially circumferentially surround and/or enclose the pressure sensing element 220, wire bonds 230, bond pads, the force transmitting member 250, and/or other components of the pressure sensor 200. The sidewall 240 may have a cross-section substantially circular or any other suitable shape. The sidewall 240 may be connected to the substrate 210 such that the second end of the sidewall 242 may face the substrate 210 and the first end of sidewall 240 may be spaced away from the substrate 210. In some cases, the sidewall 240 may be attached to at least a portion of the substrate 210 to provide additional structural integrity to the pressure sensor 200. The first end of the sidewall 241 may be positioned substantially adjacent the receiving face of the pressure sensor 201 and may at least partially define an opening from the first end of the sidewall 241 to the pressure sensing element 220 (e.g., a reservoir defined by the sidewall 240). The sidewall 240 may be made from any type of material. In one example, the sidewall 240 may be made from a plastic, a metal, a ceramic and/or any other suitable material.

In various embodiments, the force transmitting member 250 of the pressure sensor 200 may comprise a first end and a second end, wherein the first end may be configured to entirely engage a portion of the outer wall of the fluid delivery conduit 120 positioned within the gap 114 and the second end may be configured to interact with the pressure sensing element 220. The force transmitting member 250 may fill or at least partially fill the opening and/or reservoir of the sidewall 240. In various embodiments, the force transmitting member 250 may be configured to facilitate transferring a force interacting with the first end of the force transmitting member 250 to the pressure sensing element 220. In such an exemplary configuration, the force experienced by the pressure sensing element 220 may arise due to a change in pressure within the fluid delivery conduit 120 caused by a low pressure event (e.g., occlusion) and may result in a shift in the DC signal produced by the pressure sensor 200.

The force transmitting member 250 may be formed from one or more layers of material. For example, the force transmitting member 250 may be formed from one layer of material, two layers of material, three layers of material, four layers of material, five layers of material, or other number of layers of material. The force transmitting member 250 may be made from any suitable material. In various embodiments, the force transmitting member 250 may comprise a dielectric material, a non-compressible material, a biocompatible material, colored material, non-colored material, and/or one or more other types of material. Further, in various embodiments the force transmitting member 250 may comprise a gel (e.g., a fluoro-silicone gel), a resilient material such as a cured silicone rubber or silicone elastomer, a cured liquid silicone rubber, an oil and/or any other suitable material. In various embodiments, the force transmitting member 250 may include a biocompatible material such as, for example, a cured silicone elastomer, that is medically safe to directly contact medicines or the like that are to be provided to a patient. In various embodiments wherein the force transmitting member 250 comprises a gel, the pressure sensor may further comprise a membrane configured to cover the entirety of the opening at the first end of the sidewall 240 so as to contain the gel within the cavity.

In various embodiments, the force transmitting member 250 may act as a high pass filter, wherein the force transmitting member 250 may be configured to dampen low frequency events while allowing high frequency events, such as, for example, ultrasonic signals emitted from the ultrasonic transmitter 300, to pass through undisturbed while experiencing minimal or no deflection. In various embodiments, the force transmitting member 250 may act as a filter with respect to frequencies, for example, lower than approximately 100 Hz. Such a configuration, as shown in FIG. 3, allows the signals traveling from the ultrasonic transmitter 300 through the fluid delivery conduit 120 and to the pressure sensing element 220.

In various embodiments, the pressure sensor 200 may be electronically connected to the internal controller 140 such that the internal controller 140 transmits a power signal to the pressure sensor 200. In various embodiments, the pressure sensor 200 may be powered at a voltage of between 2.5 volts and 10 volts (e.g., 5 volts). The pressure sensor 200 may be configured to, upon sensing both a pressure sensor signal created by a pressure differential within the fluid delivery conduit 120 and a high frequency ultrasonic waves from the ultrasonic transmitter 300, transmit an output signal comprising both an AC component and a DC component to the internal controller 140.

As just one example, the pressure sensor 200 may comprise a Honeywell Combi® Pressure Sensor or any other suitable sensor having a configuration as described herein.

Ultrasonic Transmitter

As shown in FIGS. 1-4, the fluid flow sensor 10 may comprise an ultrasonic transmitter 300, which, in various embodiments, may be coupled to the interior portion of the housing 110. The ultrasonic transmitter 300 may define an emitting face 301 and may be arranged such that the emitting face 301 is aligned with and facing the receiving face of the pressure sensor 201. The emitting face of the ultrasonic transmitter 301 may be spaced apart from the receiving face of the pressure sensor 201 at a distance defining the gap 114. As illustrated in FIGS. 3 and 4, the ultrasonic transmitter 300 may be configured to generate and emit an ultrasonic signal in a direction substantially perpendicular to the emitting face 301, through the fluid delivery conduit 120, and towards the receiving face of the pressure sensor 201 such that the signal may be detected by the pressure sensing element 220.

As is generally understood in the art, the ultrasonic transmitter 300 may, in various embodiments, comprise an ultrasonic generator and an ultrasonic transducer. In various embodiments, the ultrasonic transducer may be, for example, a piezoelectric ultrasonic transducer. A piezoelectric ultrasonic transducer may comprise, for example, a ceramic disc (e.g., PIC255) and wrap-around electrodes configured to establish an electrical connection at a favorable position within the transducer assembly. In various embodiments, the ultrasonic transducer may have a diameter of between 2 mm and 15 mm (e.g., between 5 mm and 10 mm) and may have a thickness of between 0.5 mm and 4 mm (e.g., between 1 mm and 2 mm). In various embodiments, the ultrasonic transmitter 300 may be tuned for optimal interaction with and response by the pressure sensing element 220.

In various embodiments, the ultrasonic transmitter 300 may be electronically connected to the internal controller 140 such that the ultrasonic transmitter 300 may be powered by the internal controller 140. The internal controller 140 may be configured to further supply the ultrasonic transmitter 300 with a fixed frequency drive signal generally in the form of an oscillating signal, such as a sine-wave, square wave, triangular wave, sawtooth wave, and/or the like. However, it should be understood that other signal shapes may be provided as discussed herein. In various embodiments, the drive signal sent from the internal controller 140 to the ultrasonic transmitter 300 may manifest as a voltage centered between 2.5 volts and 10 volts (e.g., 5 volts). The ultrasonic transmitter 300 may be configured to receive the signal from the internal controller 140 and emit high frequency ultrasonic waves through the emitting face 301 and across a portion of the fluid delivery conduit 120 such that it may be received by the pressure sensor 200.

Pressure Sensing

As described herein, the fluid flow sensor 10 may be configured to detect occlusion (or other fluid pressure-changing events) within a fluid delivery conduit 120 by detecting a change in pressure within the fluid delivery conduit 120. As shown in FIGS. 2-4, the pressure sensor 200 of the fluid flow sensor 10 may be located within the interior of the housing 110 and arranged such that the receiving face of the pressure sensor 201 is at least substantially parallel and adjacent to a length of the channel 113 configured to receive and secure at least a portion of the fluid delivery conduit 120. Similarly, the emitting face of the ultrasonic transmitter 301 may be positioned at least substantially parallel to both the receiving face of the pressure sensor 201 and the length of the channel 113 configured to receive and secure at least a portion of the fluid delivery conduit 120. In such an exemplary configuration, the pressure sensor 200 (e.g., the receiving face of the pressure sensor 200) engages a portion of the outer wall of the fluid delivery conduit 120 located within the interior portion of the housing 110 such that pressure within the fluid delivery conduit 120 may exert a force onto the receiving face of the pressure sensor 201. The force exerted on the pressure sensor 200 may be detected by the force transmitting member 250, which may be configured to transmit at least a portion (e.g., all) of the force to the pressure sensing element 220. In various embodiments, the force transmitting member 250 may comprise, for example, a gel.

As described above, the pressure sensing element 220 may be configured to receive high frequency signals (e.g., oscillating signals) emitted by the ultrasonic transmitter 300. The signal emitted by the ultrasonic transmitter 300 is received by the pressure sensing element 220 after traveling through the fluid delivery conduit 120. As described above, the force transmitting member 250 may act as a high pass filter, allowing high frequency events (e.g., the signal emitted from the ultrasonic transmitter 300) to pass through without causing any deflection in the force transmitting member 250 or causing any changes in force experienced by the pressure sensing element 220.

In various embodiments, as the flow of fluid remains constant within the fluid delivery conduit 120, so too does the pressure experienced by the pressure sensor 200. A change in fluid flow rate within the fluid delivery conduit 120 caused by, for example, occlusion, results in a change of pressure within the fluid delivery conduit 120, and thus, a change in force being exerted on the inner wall of the fluid delivery conduit 120, and in turn, a change in force being transmitted from the fluid delivery conduit 120 to the pressure sensor 200. The change in force arising from a change in pressure within the fluid delivery conduit 120 may define a low frequency event received by and transmitted through the force transmitting member 250 such that it may be sensed by the pressure sensing element 220. In various embodiments, a low frequency event experienced by the pressure sensing element 220 may be detected as a shift in signal detected by the pressure sensing element 220 (e.g., correlating to a DC shift). Such a change in the signal to the pressure sensing element 220 may manifest in a proportional DC shift experienced by the pressure sensor's output signal to the internal controller 140. For example, when the fluid within the fluid delivery conduit 120 experiences occlusion, the resultant decrease in pressure leads to a decreased signal voltage output by the pressure sensing element, and thus, a negative vertical shift of the output signal. Accordingly, in various embodiments, the fluid flow sensor 10 may be configured to detect a change in pressure within a fluid delivery conduit 120 by receiving the emitted high frequency signal components from the ultrasonic transmitter 300 and correlating a detected variance in voltage (i.e. DC shifts) in the pressure sensor's resultant output signal to a decrease in flow rate within the fluid delivery conduit 120.

In various embodiments, to ensure accuracy of the signal detected by the pressure sensing element 220, both the receiving face of the pressure sensor 201 and the emitting face of the ultrasonic transmitter 301 may be positioned at least substantially parallel to and in contact with a portion of the outer wall of the fluid delivery conduit 120 secured within the channel 113. As described above and as shown in FIGS. 3 and 4, the fluid delivery conduit 120 may be compressed in the direction of the conduit's width such that the entirety of receiving face of the pressure sensor 201 is in contact with a portion of the outer wall of the fluid delivery conduit 120. Such a configuration enables the entirety of the face of the force transmitting member 250 to be coupled to the surface of the fluid flowing through the fluid delivery conduit 120 for the purposes of sensing force, and prevents any undesirable force "leakage" that is transmitted away from the pressure sensing element 220. In various embodiments, failure to fully cover the face of the pressure sensor with an adjacent portion of the fluid delivery conduit 120, and thus failure to essentially couple the pressure sensing element 220 to the fluid being sensed through the force transmitting member 250, may result in the force transmitting member 250 receiving a distorted signal. Such a distortion may result in the fluid flow sensor 10 producing inaccurate readings.

Bubble Detection

As described herein, the fluid flow sensor 10 may be configured to detect the presence of an air bubble 302 within a fluid delivery conduit 120 by detecting a change in the signal (e.g., the oscillating signal component) emitted from the ultrasonic transmitter and received by the pressure sensor 200. As described above and as shown in FIGS. 3 and 4, the pressure sensor 200 of the fluid flow sensor 10 may be located within the interior of the housing 110 and arranged such that the receiving face of the pressure sensor 201 is at least substantially parallel to a length of the channel 113 configured to receive and secure at least a portion of the fluid delivery conduit 120. Similarly, the emitting face of the ultrasonic transmitter 301 may be positioned at least substantially parallel to both the receiving face of the pressure sensor 201 and the length of the channel 113 such that the emitting face of the ultrasonic transmitter 301 and the receiving face of the pressure sensor 201 are spaced apart to define a gap 114 configured to accept the fluid delivery conduit 120 therein.

In such an exemplary configuration, the ultrasonic transmitter 300 may be configured to receive a drive signal (e.g., an oscillating drive signal, such as an AC drive signal) from the internal controller 140 and to emit ultrasonic waves carrying the signal through the emitting face of the ultrasonic transmitter 301, through the portion of the fluid delivery conduit 120 positioned within the gap 114, and to the receiving face of the pressure sensor 201. In various embodiments, as described above, the force transmitting member 250 may act as a high pass filter, allowing the signal emitted from the ultrasonic transmitter 300 to pass through without causing any deflection in the force transmitting member 250 or causing any changes in force experienced by the pressure sensing element 220. In various embodiments, wherein the force transmitting member 250 may be, for example, a gel, the gel may act as an incompressible fluid. The emitted signal may be sensed by the pressure sensing element 220, which may be configured to subsequently transmit an output signal to the internal controller 140 indicative of the detected signal. As described above, the emitted signal may be embodied as an AC signal or another oscillating signal shape, centered on a voltage characterized by a DC shift in the drive signal.

In an exemplary condition wherein there are no air bubbles present within the fluid delivery conduit 120, as illustrated in FIG. 3, substantially all of the waves emitted from the ultrasonic transmitter 300 are sensed by the pressure sensor 200, resulting in a signal transmitted to the internal controller 140 that is indicative of an uninterrupted signal transmitted through the fluid delivery conduit 120. Conversely, in an exemplary condition wherein at least one air bubble 302 is present within the fluid delivery conduit 120, as illustrated in FIG. 4, the air bubble 302 may effectively act as an acoustic mirror that may reflect and/or deflect at least a portion of the emitted signal, deflecting the portion of the signal away from the pressure sensing element 220. In such an exemplary circumstance, the reflection of at least a portion of the emitted signal results in a distorted signal received by the pressure sensing element 220. When at least a portion of the signal emitted from the ultrasonic transmitter 300 is deflected before being received by the pressure sensing element 220, the received signal may exhibit, for example, a change in shape, amplitude, and/or the like detected by the pressure sensing element 220. Accordingly, in various embodiments, the fluid flow sensor 10 may be configured to detect the presence of an air bubble 302 within a fluid delivery conduit 120 by monitoring the emitted high frequency signal from the ultrasonic transmitter 300 and correlating changes in shape and/or amplitude of the resultant output signal to the presence of a bubble 302 within the fluid delivery conduit 120. Further, in various embodiments, the fluid flow sensor 10 may be further configured to determine specific characteristics about the detected bubble 302 such as, for example, its size, based on one or more of the distortions in the signal received by the pressure sensing element (e.g., a larger change in amplitude of the detected signal may correlate to a larger bubble size).

Experimental Testing

Experimental testing was conducted to verify the effectiveness of embodiments as described herein. Data was collected over the course of multiple trials using various combinations of embodiments described above.

In the testing configuration, an exemplary fluid flow sensor used for testing was configured to be in electronic communication with both the pressure sensor controller and the ultrasonic transmitter controller. The pressure sensor controller was configured to transmit a power signal to the pressure sensor. Similarly, the ultrasonic transmitter controller was configured to transmit a power signal to the ultrasonic transmitter. The testing circuitry comprised a drive circuit configured to transmit a signal to the ultrasonic transmitter. The shape of the drive signal may be determined, at least in part, by the configuration of the drive circuit. The testing circuitry was further electronically connected to an oscilloscope configured to generate the drive signal and graphically display both the ultrasonic transmitter drive signal and the output signal sensed by the pressure sensor. Example drive signals 460 and example output signals 470, 480 are shown in FIGS. 7 and 8.

Figure 6:
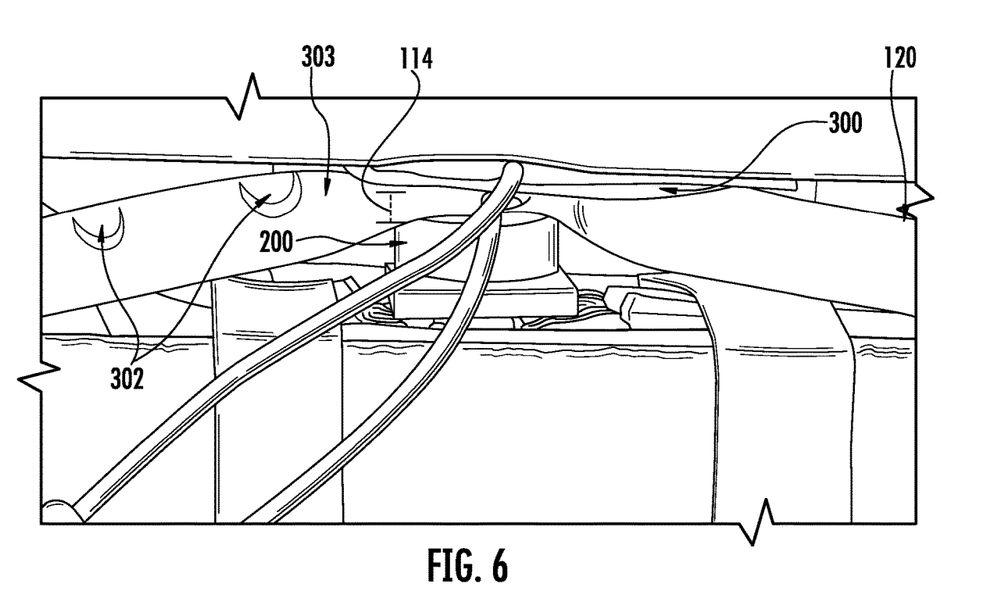
FIG. 6 shows an exemplary test configuration in accordance with various embodiments.

FIG. 6 shows a close-up view of the fluid flow sensor 10 sensory components used in the exemplary testing configuration. The pressure sensor 200 is secured to the bottom surface of a vise, a configuration meant to recreate the mounting of the pressure sensor 200 within the interior portion of the housing 110. Similarly, the ultrasonic transmitter 300 is secured relative to the top surface of the vise. In such a configuration, the pressure sensor 200 and the ultrasonic transmitter 300 are spaced apart so as to define a gap 114 configured to receive a portion of the fluid delivery conduit 120. As shown in FIG. 6, the testing configuration comprised the pressure sensor 200 and the ultrasonic transmitter 300 mounted to a vise so as to replicate the requisite compression applied to the fluid delivery conduit 120 when secured within the housing 100 of the fluid flow sensor 10. As described above, the fluid delivery conduit 120 was compressed by the vise such that the entirety of the receiving face of the pressure sensor 201 was covered by at least a portion of the outer wall of the fluid delivery conduit 120.

The exemplary testing configuration utilized a fluid 303 flowing through the tube with deliberately injected air bubbles 302 present within the fluid delivery conduit 120 to enable analysis of the signal sensed by the pressure sensor 200 under conditions both with and without air bubbles 302 present within the fluid delivery conduit 120.

Figure 7:
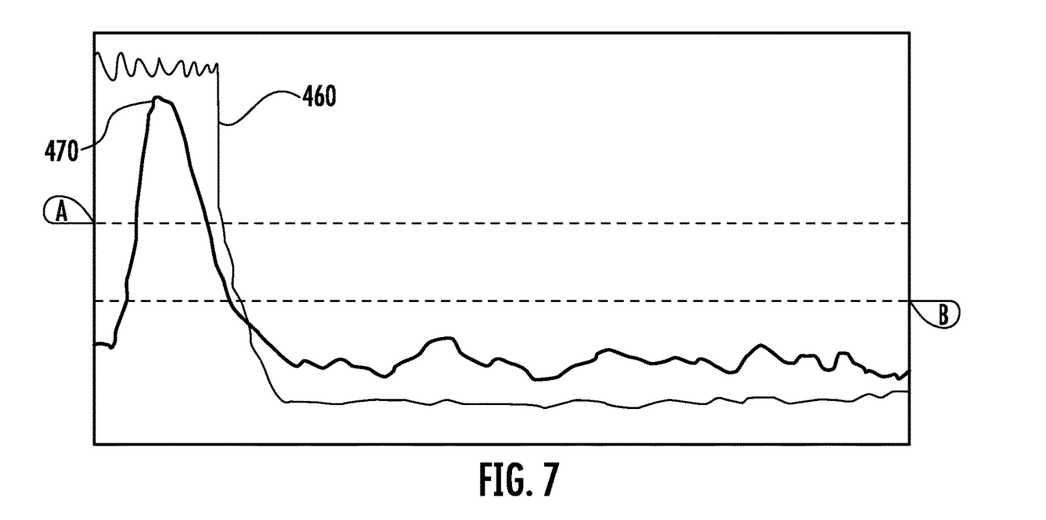
FIG. 7 shows an exemplary graphical representation of signals produced by a testing configuration in accordance with various embodiments.
Figure 8:
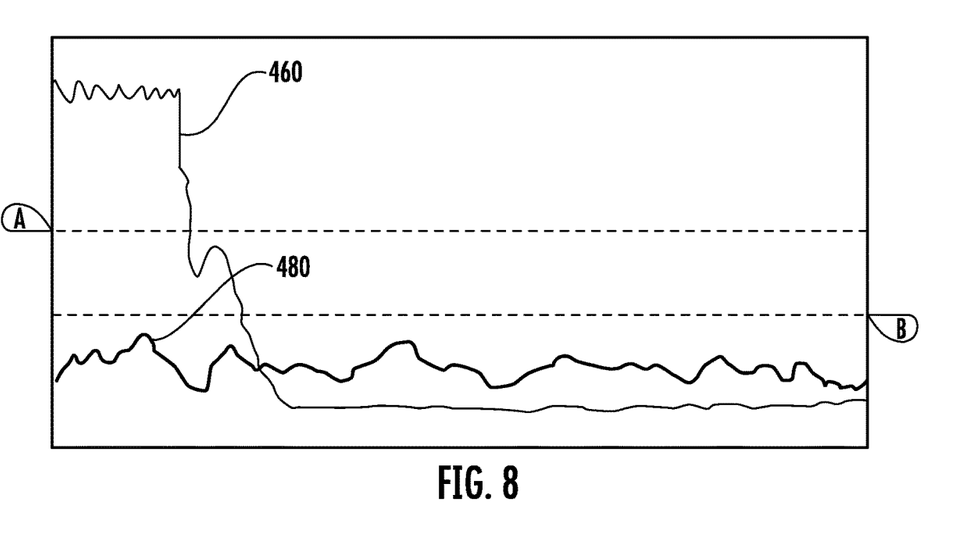
FIG. 8 shows an exemplary graphical representation of signals produced by a testing configuration in accordance with various embodiments.

FIG. 7 shows a graphical representation of a single wave of an example ultrasonic transmitter 300 drive signal 460 (which may encompass a repeating, periodic waveform), as well as an example output signal wave sensed by a pressure sensor 470 under baseline fluid flow conditions. As described above, the characteristics of the ultrasonic transmitter drive signal 460 may be selected to produce a drive signal shape for use in conjunction with the specific testing circuitry. Here, the shape of the example ultrasonic transmitter drive signal 460—shown in FIGS. 7 and 8—is similar to that of a general AC signal, but noticeably may have a substantially flattened top rather than the typical rounded wave shape of a sine wave. The shape of the example output signal 470—shown in FIG. 7—may vary from that shown therein, and generally correlates to a baseline fluid pressure within a fluid delivery conduit void of air bubbles. As shown, the example output signal 470 is centered around an axis B, which may represent a signal shift of, for example, 10 mV. Upon detection of a change in pressure, the output signal 470 may shift vertically to represent the change in pressure. The exemplary ultrasonic transmitter drive signal 460 as illustrated is centered at an exemplary axis A, correlating to an input of, for example, approximately 5 V. Further, in various embodiments, the drive signal 460 may have a frequency of, for example, about 130 kHz, although it should be understood that other frequencies above the high-pass filter cutoff of the force transmitting member 250 may be utilized. As described above, a DC shift of the output signal 470 may correspond to a change in pressure within the fluid delivery conduit 120 due to, for example, occlusion.

FIG. 8 shows a graphical representation of a single wave of an example ultrasonic transmitter 300 drive signal 460, as well as an exemplary distorted output signal wave sensed by the pressure sensor 480, caused by the presence of a gas bubble within a fluid delivery conduit 120. As described above, in a condition in which gas bubbles 302 are present within the fluid delivery conduit 120, the output signal 480 may exhibit characteristics different from those of the output signal under normal baseline fluid flow conditions 470. For example, as shown in FIG. 8, the presence of air bubbles 302 within a testing fluid delivery conduit 120 may result in a signal shift of, for example about 5 mV, highlighted by the fact that the respective maximums of the signal waves (i.e. signals 470 and 480) are noticeably lower when measured in the presence of an in-line air bubble.

As described herein, the fluid flow sensor 10 is configured so as to enable the simultaneous monitoring of both the AC and DC components of the pressure sensor output signal. Critically, such a configuration may effectively reduce the error rate of the sensor by compensating for unwarranted external forces that may affect the sensor's acoustic baseline and lead in inaccuracies. Such a shift of the sensor's acoustic baseline may be caused by factors such as, for example, tubing/plastic deformation, temperature change, and/or fluid pressure that result in an unwarranted change of contact force to the sensor. Configuring the components of the fluid flow sensor in such a way that enables the coupling of the AC and DC components enables the efficient and accurate characterization of flow within a fluid delivery conduit.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A fluid flow sensor, the sensor comprising:
    an ultrasonic transmitter configured to emit ultrasonic signals through an emitting face; and
    a pressure sensor configured to detect pressure changes through a receiving face;
    wherein the emitting face of the ultrasonic transmitter is spaced apart from the receiving face of the pressure sensor to collectively define a gap configured to receive a fluid delivery conduit therein;
    wherein at least substantially all of the receiving face of the pressure sensor is in contact with a portion of the fluid delivery conduit;
    wherein a width of the gap is smaller than a width of the fluid delivery conduit causing a compression force to be applied to at least a portion of an outer wall of the fluid delivery conduit positioned within the gap such that the entirety of the receiving face of the pressure sensor is in contact with the portion of the outer wall of the fluid delivery conduit; and
    wherein the pressure sensor is configured to:
        detect a change in pressure within a fluid delivery conduit positioned within the gap; and
        receive ultrasonic signals from the ultrasonic transmitter to detect bubbles flowing through the fluid delivery conduit positioned within the gap.

2. The fluid flow sensor of claim 1, further comprising a housing, wherein the housing comprises an exterior housing portion and an interior housing portion, and wherein the ultrasonic transmitter and the pressure sensor are enclosed within the interior housing portion.

3. The fluid flow sensor of claim 2, wherein the interior housing portion further defines a channel configured to secure at least a portion of the fluid delivery conduit within the interior portion of the housing and wherein at least a portion of the channel is aligned with the gap.

4. The fluid flow sensor of claim 1, wherein the pressure sensor comprises:
    a pressure sensing element mounted to a substrate; and
    a force transmitting member positioned adjacent to the pressure sensing element, wherein the force transmitting member transmits a force applied to the front side of the force transmitting member to the front side of the pressure sensing element.

5. The fluid flow sensor of claim 4, wherein the force transmitting member is a gel.

6. The fluid flow sensor of claim 1, wherein an internal controller is configured for wireless communication of an output signal.

7. The fluid flow sensor of claim 1, wherein the ultrasonic transmitter is configured to receive a drive signal from an internal controller, wherein the drive signal comprises at least one of an AC component or a DC component.

8. The fluid flow sensor of claim 1, wherein the ultrasonic transmitter comprises a piezoelectric ultrasonic transducer.

9. The fluid flow sensor of claim 8, wherein the ultrasonic transmitter further comprises an ultrasonic generator.

10. The fluid flow sensor of claim 1, wherein the fluid flow sensor is configured to detect a change in pressure within the fluid delivery conduit based at least in part on a detected shift in a received signal.

11. The fluid flow sensor of claim 1, wherein the fluid flow sensor is configured to detect an air bubble within the fluid delivery conduit based at least in part on a detected change in ultrasonic signal amplitude received from the ultrasonic transmitter.

12. A method of detecting occlusion and the presence of bubbles within a fluid delivery conduit, the method comprising:
    detecting a change in pressure within the fluid delivery conduit based at least in part on a detected shift in a received signal; and
    detecting an air bubble within the fluid delivery conduit based at least in part on a detected change in ultrasonic signal amplitude received from a ultrasonic transmitter;
    wherein an output signal of a pressure sensor comprises an AC component and a DC component;
    wherein the fluid delivery conduit is positioned between a receiving face of the pressure sensor and the ultrasonic transmitter;
    wherein an emitting face of the ultrasonic transmitter is spaced apart from the receiving face of the pressure sensor to collectively define a gap configured to receive the fluid delivery conduit therein;
    wherein a width of the gap is smaller than a width of the fluid delivery conduit causing a compression force to be applied to at least a portion of an outer wall of the fluid delivery conduit positioned within the gap such that the entirety of the receiving face of the pressure sensor is in contact with the portion of the outer wall of the fluid delivery conduit; and
    wherein at least a portion of the fluid delivery conduit is compressed in a direction of a width of the fluid delivery conduit such that at least substantially all of the receiving face of the pressure sensor is in contact with a portion of the fluid delivery conduit.

13. The method of claim 12, further comprising emitting ultrasonic signals from the ultrasonic transmitter, through the fluid delivery conduit, and to the pressure sensor aligned with the ultrasonic transmitter on an opposite side of the fluid delivery conduit and configured to receive the ultrasonic signals emitted from the ultrasonic transmitter.

14. The method of claim 13, further comprising receiving, by the ultrasonic transmitter, an AC drive signal from an internal controller, wherein the ultrasonic signals emitted from the ultrasonic transmitter comprises the AC drive signal.

15. The method of claim 12, wherein a DC shift in the output signal of the pressure sensor corresponds to a change in pressure within the fluid delivery conduit.

16. The method of claim 12, further comprising communicating the output signal of the pressure sensor to one or more external devices.

17. The method of claim 16, wherein an internal controller is configured for wireless communication of an output signal.

* * * * *